| United States Patent [19] | [11] | 4,217,301 |
|---|---|---|
| Siegrist et al. | [45] | Aug. 12, 1980 |

[54] CYANO-SUBSTITUTED STILBENE COMPOUNDS

[75] Inventors: Adolf E. Siegrist, Basel; Vincenzo Coviello, Marly, both of Switzerland

[73] Assignee: Ciba-Geigy Corporation, Ardsley, N.Y.

[21] Appl. No.: 887,108

[22] Filed: Mar. 16, 1978

Related U.S. Application Data

[62] Division of Ser. No. 723,691, Sep. 16, 1976, Pat. No. 4,097,515, which is a division of Ser. No. 519,164, Oct. 30, 1974, Pat. No. 4,008,224.

[30] Foreign Application Priority Data

Nov. 19, 1973 [CH] Switzerland ...................... 16246/73
Nov. 19, 1973 [CH] Switzerland ...................... 16247/73

[51] Int. Cl.$^2$ ........................................... C07C 121/60
[52] U.S. Cl. ........................... 260/465 G; 252/301.21; 252/301.22; 252/301.35; 260/465 H; 260/465 K; 260/566 R; 427/158; 542/415; 542/422; 542/454; 542/459

[58] Field of Search ...................... 260/465 G, 465 K; 252/301.21

[56] References Cited

U.S. PATENT DOCUMENTS

| 3,984,339 | 10/1976 | Weber et al. ......................... 260/465 |
| 3,991,049 | 11/1976 | Siegrist et al. .............. 252/301.22 X |

FOREIGN PATENT DOCUMENTS 1131484 10/1968 United Kingdom .
1222863 2/1972 United Kingdom .

OTHER PUBLICATIONS

Becker, J. Org. Chem., vol. 29, pp. 2891-2894, (1964).

Primary Examiner—Dolph H. Torrence
Attorney, Agent, or Firm—Prabodh I. Almaula

[57] ABSTRACT

A new process for the manufacture of cyano-substituted stilbene compounds, new stilbene compounds as well as their use as fluorescent brighteners or as intermediates for the manufacture of fluorescent brighteners are provided.

3 Claims, No Drawings

CYANO-SUBSTITUTED STILBENE COMPOUNDS

This is a divisional application of application Ser. No. 723,691, filed Sept. 16, 1976, now U.S. Pat. No. 4,097,515, issued June 26, 1978, which is a divisional of Ser. No. 519,164, filed Oct. 30, 1974, now U.S. Pat. No. 4,008,224, issued Feb. 15, 1977.

The present invention relates to the manufacture of cyano-substituted stilbene compounds, to new cyano-substituted stilbene compounds and to their use as fluorescent brighteners for organic materials of high molecular weight or as intermediates for the manufacture of fluorescent brighteners.

The manufacture of stilbene derivatives by the anil synthesis is taught in British Pat. Nos. 1,131,484 and 1,222,803.

The surprising discovery has now been made that, by means of the anil synthesis, it is possible to react toluene derivatives which are substituted in a very specific manner by the cyano group to yield stilbene derivatives, with retention of the cyano group.

The present invention provides a process for the manufacture of cyano- substituted stilbene compounds of the formula

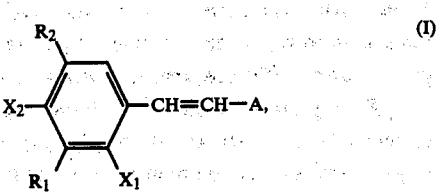

wherein either $X_1$ represents the cyano radical and $X_2$ represents hydrogen, chlorine or fluorine or together with $R_1$ represents a fused benzene ring, or $X_2$ represents the cyano radical and $X_1$ represents hydrogen, chlorine or alkyl with 1 to 4 carbon atoms or together with $R_1$ represents a fused benzene ring, $R_1$ represents hydrogen, chlorine, fluorine or alkoxy with 1 to 4 carbon atoms or together with $X_1$ or $X_2$ represents a fused benzene ring, $R_2$ represents hydrogen, chlorine, fluorine or alkoxy with 1 to 4 carbon atoms and A represents a phenyl, naphthyl, biphenyl, stilben-4-yl, dibenzofuran-3-yl, 4-(benzo [b] furan-2-yl)-phenyl or 2-phenyl-benzo [b] furan-6-yl radical, which is unsubstituted or substituted by chlorine and/or alkoxy with 1 to 4 carbon atoms or a radical of the formula

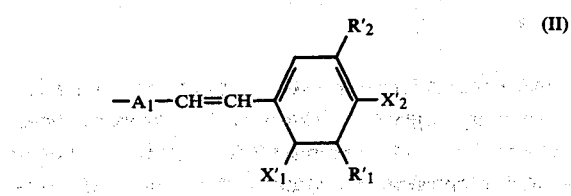

wherein either $X_1'$ represents the cyano radical and $X_2'$ represents hydrogen, chlorine, or fluorine or $X_2'$ represents the cyano radical and $X_1'$ represents hydrogen, chlorine or alkyl with 1 to 4 carbon atoms, each of $R_1'$ and $R_2'$ independently represents hydrogen, chlorine, fluorine or alkoxy with 1 to 4 carbon atoms and $A_1$ represents 1,4-, 1,5- or 2,6- naphthylene, 1,4- phenylene or 4,4'- bisphenylene which comprises reacting a toluene derivative of the formula

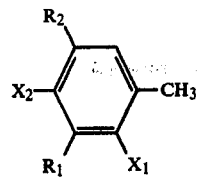

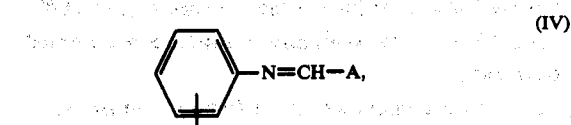

wherein $X_1$, $X_2$, $R_1$ and $R_2$ have the meaning given above with, a Schiff's base of the formula

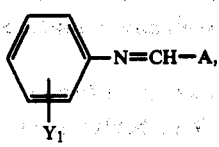

wherein $Y_1$ represents chlorine or hydrogen, preferably in the 2- position, and A has the meaning given above, in dimethyl formamide and in the presence of sodium alcoholate at a temperature of 0° to 40° C.

In a first aspect of the present invention provides a process for the manufacture of cyanosubstituted stilbene compounds of the formula

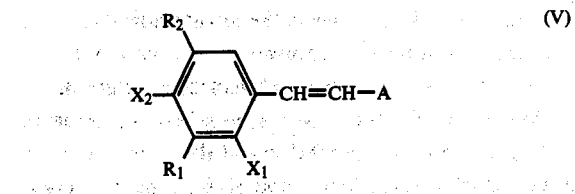

wherein either $X_1$ represents the cyano radical and $X_2$ represents hydrogen, chlorine or fluorine or together with $R_1$ represents a fused benzene ring, or $X_2$ represents the cyano radical and $X_1$ represents hydrogen, chlorine or alkyl with 1 to 4 carbon atoms or together wit $R_1$ represents a fused benzene ring, $R_1$ represents hydrogen, chlorine, fluorine or alkoxy with 1 to 4 carbon atoms or together with $X_1$ or $X_2$ represents a fused benzene ring, $R_2$ represents hydrogen, chlorine, fluorine or alkoxy with 1 to 4 carbon atoms and A represents a phenyl, naphthyl, biphenyl, stilben-4-yl, dibenzofuran-3-yl, 4-(benzo [b]furan-2-yl)-phenyl or 2-phenyl-benzo[b]furan-6-yl radical which is optionally substituted by chlorine and/or alkoxy with 1 to 4 carbon atoms, which process comprises reacting a compound of the formula

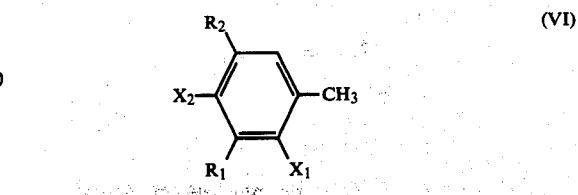

wherein $X_1$, $X_2$, $R_1$ and $R_2$ have the meanings assigned to them hereinbefore, with a Schiff's base of the formula

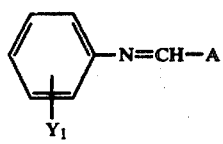
(VII)

wherein $Y_1$ represents chlorine or hydrogen and A has the meaning given above.

Preferred alkyl and alkoxy substituents are respectively methyl and methoxy. Fluorine represented by $X_2$, $R_1$ and $R_2$ is of less significance than the other cited substituents.

Some of the compounds of the formula (V) are novel and some are known. Of particular interest is the manufacture of compounds of the formula

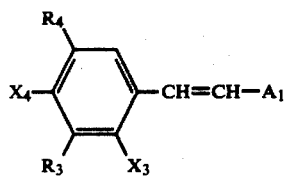
(VIII)

wherein either $X_3$ represents the cyano radical and $X_4$ represents hydrogen or chlorine or $X_4$ represents the cyano radical and $X_3$ represents hydrogen, chlorine or methyl, each of $R_3$ and $R_4$ independently represents hydrogen, chlorine or methoxy and $A_1$ represents a phenyl, naphthyl, biphenyl, stilben-4-yl, dibenzofuran-3-yl, 4-(benzo [b] furan -2-yl)-phenyl or 2-phenylbenzo[b]-furan-6-yl radical which is optionally substituted by chlorine or methoxy, which comprises reacting a compound of the formula

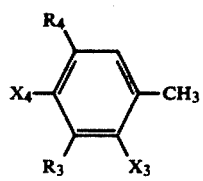
(IX)

wherein $R_3$, $R_4$, $X_3$ and $X_4$ have the meanings assigned to them hereinbefore, with a Schiff's base of the formula

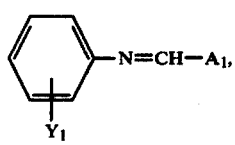
(X)

wherein $Y_1$ and $A_1$ have the meanings previously assigned to them.

Compounds having a praticularly interesting utility are the novel compounds of the formula

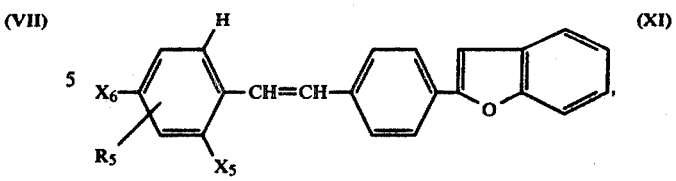
(XI)

wherein either $X_5$ represents the cyano radical and $X_6$ represents hydrogen or chlorine or $X_6$ represents the cyano radical and $X_5$ represents hydrogen, chlorine or methyl and $R_5$ represents hydrogen or chlorine, but one of the symbols $X_5$, $X_6$ and $R_5$ must be hydrogen.

Novel compounds are also those of the formula

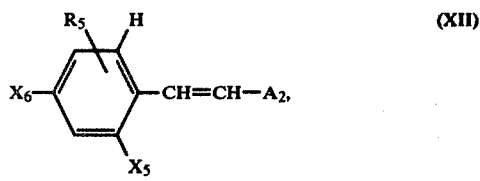
(XII)

wherein either $X_5$ represents the cyano radical and $X_6$ represents hydrogen or chlorine or $X_6$ represents the cyano radical and $X_5$ represents hydrogen, chlorine or methyl, $R_5$ represents chlorine or hydrogen and $A_2$ represents a dibenzo-furan-3-yl or 2- phenyl-benzo[b]furan-6-yl radical and the compound of the formula

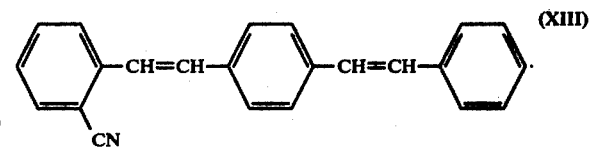
(XIII)

Compounds falling within the scope of the formula (V) are also those of the formula

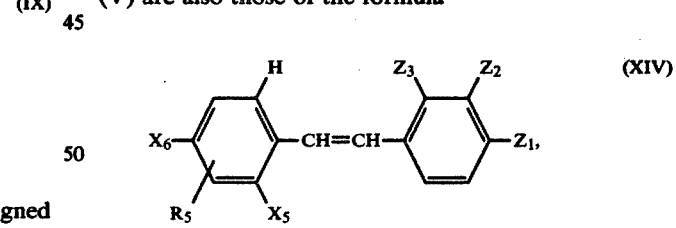
(XIV)

wherein either $X_5$ represents the cyano radical and $X_6$ represents hydrogen or chlorine or $X_6$ represents the cyano radical and $X_5$ represents hydrogen, chlorine or methyl, $R_5$ represents hydrogen or chlorine, $Z_1$ represents hydrogen, chlorine or phenyl or together with $Z_2$ represents a fused benzene ring, $Z_2$ represents hydrogen or together with $Z_1$ or $Z_3$ represents a fused benzene ring and $Z_3$ represents hydrogen or together with $Z_2$ represents a fused benzene ring.

The compounds of the formula (XI) to (XIV) are obtained according to the invention by reacting a toluene derivative of the formula

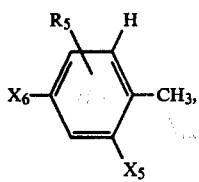 (XV)

wherein $X_5$, $X_6$ and $R_5$ have the meanings previously assigned to them, with a Schiff's base of the formulae

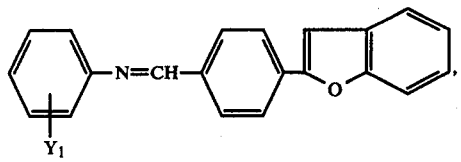 (XVI)

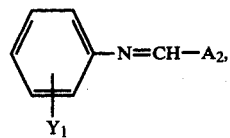 (XVII)

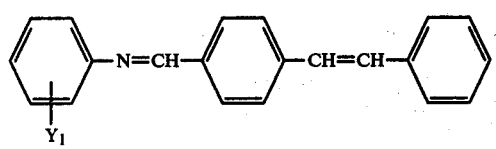 (XVIII)

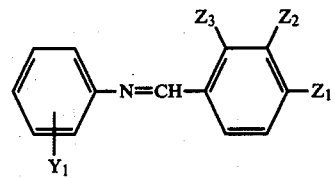 (XIX)

wherein $Y_1$, $Z_1$, $Z_2$, $Z_3$ and $A_2$ have the respective meanings previously assigned to them.

The reaction products can be processed from the reaction mixture by conventional methods which are known per se.

The cyano-substituted toluene derivatives of the formulae (VI), (IX) and (X) are known or are manufactured by processes which are known per se.

The Schiff's bases of the formulae (VII), (X), (XVI), (XVII), (XVIII) and (XIX) are also known and/or are obtained in known manner by reaction of the corresponding aldehyde, i.e. an aldehyde of the formula

A—CHO (XX)

with an aniline of the formula

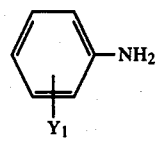 (XXI)

As a rule, equivalent amounts to double to the equivalent amounts of toluene derivative are used, based on the Schiff's bases, i.e. 1 to 2 moles of toluene derivative per mole of Schiff's base.

Normally, at least the equivalent amount of alcoholate is used, i.e. at least 1 mole per mole of Schiff's base. However, a surplus of alcoholate is used with advantage, for example up to 6 moles per mole of Schiff's base.

The compunds of the formulae (V), (VIII), (XI), (XII), (XIII) and (XIV) can be used for treating organic materials of high molecular weight with fluorescent brighteners. The compounds of the formula (XIV) exhibit in general no absolute maxium effect. However, these compounds are eminently suitable for the manufacture of higher molecular fluorescent brighteners (e.g. benzoxazoles according to U.S. Pat. No. 2,995,564); accordingly, they constitute useful intermediates.

Particularly effective fluorescent brighteners are embraced by the formula (XI). These compounds are therefore principally suitable for brightening polyester and polypropylene. The fluorescent brighteners can be incorporated into the polyester and polypropylene spinning masses or they can later be applied to the finished fibres, e.g. in woven textiles, by means of the exhaustion or padding process, in particular by the pad-heat process. The compound of the formula (XIII) exhibits outstanding effects especially on polypropylene.

As a rule, 0.001 to 2%, preferably 0.01 to 0.5%, of fluorescent brightener, based on the weight of the polymer, is incorporated into the fibres or applied thereto.

In a second aspect the present invention provides a process for the manufacture of cyano-substituted silbene compounds of the formula

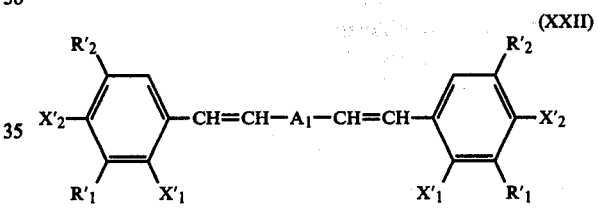 (XXII)

wherein $A_1$ represents 1,4-, 1,5- or 2,6-naphtylene, 1,4-phenylene or 4,4'-bisphenylene, either $X'_1$ represents the cyano radical and $X'_2$ represents hydrogen, chlorine or fluorine or $X'_2$ represents the cyano radical and $X'_1$ represents hydrogen, chlorine or alkyl with 1 to 4 carbon atoms, each of $R'_1$ and $R'_2$ independently represents hydrogen, chlorine, fluorine or alkoxy with 1 to 4 carbon atoms, which comprises reacting a toluene derivative of the formula

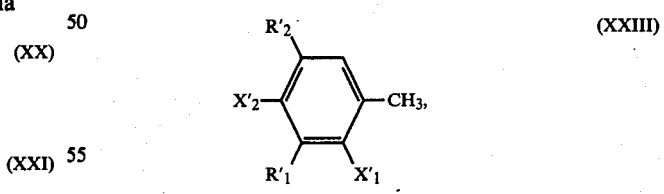 (XXIII)

wherein $X'_1$, $X'_2$, $R'_1$ and $R'_2$ have the meanings assigned to them hereinbefore, with a Schiff's base of the formula

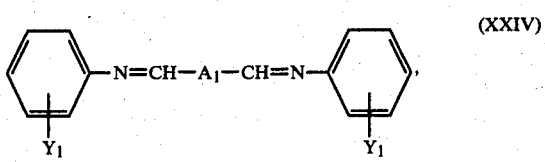 (XXIV)

wherein $Y_1$ represents chlorine or hydrogen, preferably chlorine in the 2-position, and $A_1$ has the meaning previously assigned to it.

The preferred naphthylene radical is the 2,6-naphthylene radical. Preferred alkyl and alkoxy are respectively methyl and methoxy. Fluorine represented by $X'_2$, $R'_1$ and $R'_2$ is of less significance than the other indicated possibilities.

The compounds of the formula (XXII) which contain in addition to the abligatory cyano radical one or more substituents which are different from hydrogen of the kind defined in respect of $X'_1$, $X'_2$, $R'_1$ and $R'_2$ are novel. Novel compounds with a particularly interesting utility have the formula

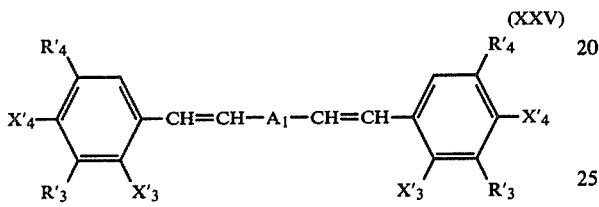
(XXV)

wherein one of the symbols $X'_3$ and $X'_4$ represents the cyano radical and the other represents hydrogen or chlorine, and each of $R'_3$ and $R'_4$ independently represents hydrogen or chlorine, but at least one, and at most two, of the symbols $X'_3$, $X'_4$, $R'_3$ and $R'_4$ represents chlorine, and wherein $A_1$ has the meaning previously assigned to it.

Of primary interest within the scope of the formula (XXV) are the compounds of the formula

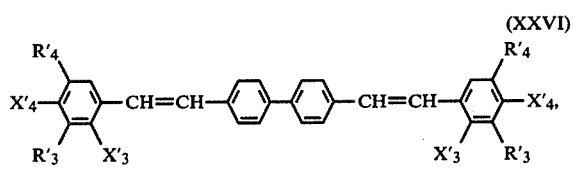
(XXVI)

wherein $X'_3$, $X'_4$, and $R'_3$ and $R'_4$ have the meanings previously assigned to them.

The preferred compounds of the formulae (XXV) and (XXVI) are those in which $X'_3$ represents the cyano radical.

Compounds of the formula

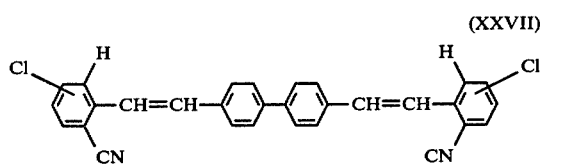
(XXVII)

have a particularly interesting utility in respect of their application for treating spinning masses, especially those on a polyester basis, with fluorescent brighteners.

The compounds of the formulae (XXV) to (XXVII) are obtained according to the invention by reaction of a toluene derivative of the formula

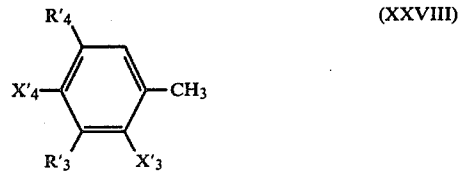
(XXVIII)

or

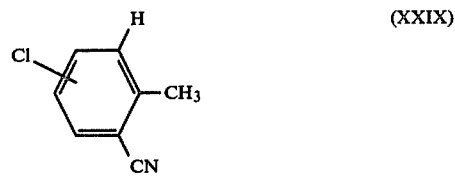
(XXIX)

with a Schiff's base of the formula (XXIV) or of the formula

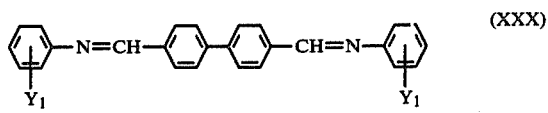
(XXX)

wherein $Y_1$ has the meaning assigned to it hereinbefore.

In general, there are used equivalent to double the equivalent amounts of toluene derivative based on the amount of Schiff's base, i.e. 2 to 4 moles of toluene derivative for each mole of Schiff's base. Normally, at least the equivalent amount of alcohol is used, i.e. at least 2 moles per mole of Schiff's base. However, it is advantageous to use an excess of alcoholate, for example up to 12 moles per mole of Schiff's base.

The final products can be processed from the reaction mixture by conventional methods which are known per se.

The compounds of the formulae (XXII) and (XXV) to (XXVII) defined hereinbefore can be used for the fluorescent brightening of organic materials of high molecular weight. They are particularly suitable for spinning masses, in particular for polyester spinning masses. As a rule, 0.001 to 2 percent by weight preferably 0.01 to 0.5 percent by weight of fluorescent brightener of the formula (XXII) or (XXV) to (XXVII), based on the weight of the polymer, is added to the spinning melts or solutions.

The reaction according to the invention of the cyano-substituted toluene derivative with the Schiff's base is carried out in the presence of dimethyl formamide as solvent and of sodium alcoholates, for instance those of the formula $$NaOC_nH_{2n+1}$$ (XXXI)

wherein n is an integer from 1 to 5. Examples of such sodium alcoholates are sodium methylate, sodium ethylate, sodium isopropylate, sodium tert butylate. The use of sodium methylate is preferred. It is, of course, also possible to use mixture of such alcoholates.

The process according to the invention is advantageously carried out excluding air at temperatures between 0° to about 40° C., preferably between 15° and 30° C. On carrying out the reaction at room temperature, no external supply of heat is necessary. As a rule, the reaction time is from ½ hour to 24 hours.

The following Examples illustrate the invention without being in any way limitative thereof.

EXAMPLE 1

5.86 g of p-tolunitrile, 14.59 g of the Schiff's base from p-chloroaniline and diphenyl-4-carbaldehyde, and 4.5 g of sodium methylate are stirred in 100 ml of dimethyl formamide for 24 hours at 20° to 25° C, excluding air. Then 400 ml of methanol are added, the reaction mixture is cooled to 0° C. and the precipitated product is then collected by suction filtration, washed with 150 ml of methanol and dried, to yield 12.8 g (=90.8% of theory) of 4-cyano-4'-phenyl-stilbene of the formula

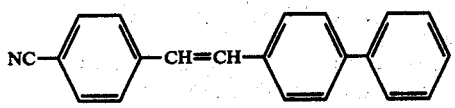
(1)

in the form of a pale yellow powder with a melting point of 235° to 254° C. (phase transition point: 194°–194.5° C.). Two recrystallisations from xylene (fuller's earth) yield 11.3 g (80.1% of theory) of colourless, thin needles of melting point 253° to 254° C. (phase transition point: 198.5° to 199° C.)

Analysis: $C_{21}H_{15}N$ (281.34): calculated: C: 89.65, H: 5.37, N: 4.98; found: C: 89.41, H: 5.32, N: 4.99.

The following stilbene derivatives can be manufactured in similar manner:

(2) 2-cyano-4'-phenyl-stilbene; melting point 136° to 136.5° C.
(3) 2-methyl-4-cyano-4'-phenyl-stilbene: melting point 180.5° to 181° C.
(4) 2-cyano-3',4'-benzo-stilbene: meltin point 116.5° to 117° C.
(5) 4-cyano-3',4'-benzo-stilbene: melting point 180.5° to 181° C.
(6) 4-cyano-2',3'-benzo-stilbene: melting point 130.5° to 131° C.
(7) 4-cyano-4'-chloro stilbene:melting point 179.5° to 180° C.
(8) 4-cyano-stilbene: melting point 117° to 117.5° C.

EXAMPLE 2

6.36 g of the Schiff's base from p-chloroaniline and stilbene-4-carbaldehyde of the formula

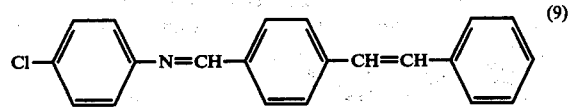
(9)

(melting point: 230° to 231° C., phase transition point: 209°–210° C.), 2.34 g of p-tolunitrile and 2.16 g of sodium methylate are reacted in 100 ml of dimethyl formamide according to the particulars of Example 1. Yield: 5.2 g (84.6% of theory) of 4-(p-cyano-styryl)-stilbene of the formula

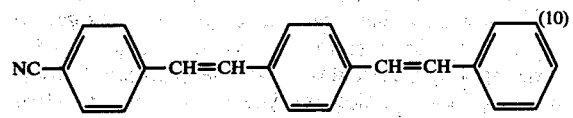
(10)

as a yellow powder with a melting point of 299° to 300° C. (phase transition point: 250° to 251° C.). Two recrystallisations from xylene (fuller's earth) yield 4.2 g (68.4% theory) of light, yellowish green, very fine needles with a melting point of 310° to 311° C. (phase transition point: 257° to 258° C.).

Analysis: $C_{23}H_{17}N$ (307.37): calculated: C: 89.86, H: 5.58, N: 4.56; found: C: 89.61, H: 5.26, N: 4.43.

The following styryl-stilbene derivatives can be manufactured in similar manner:

(11) 4-(o-cyano-styryl)-stilbene; melting point: 178° to 179° C.
(12) 4-(2-methyl-4-cyano-styryl)-stilbene; melting point 207° to 208° C.

EXAMPLE 3

7.64 g of the Schiff's base from dibenzofuran-3-carbaldehyde and p-chloroaniline of the formula

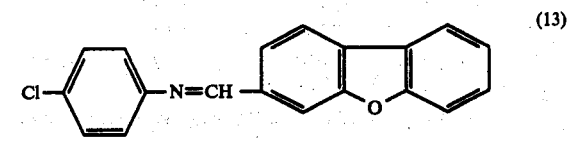
(13)

(melting point: 159° to 159.5° C.), 2.93 g of o-tolunitrile and 2.7 g of sodium methylate are reacted in 80 ml of dimethyl formamide according to the particulars of Example 1. Yield: 4.0 g (54.1 % of theory) of β-(dibenzofuran-3 yl) 2-cyano-styrene of the formula

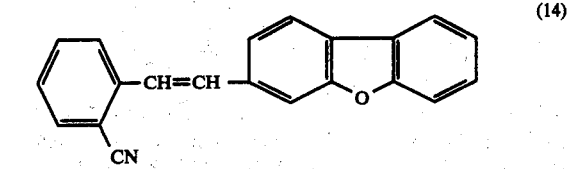
(14)

in the form of a pale yellow powder with a melting point of 143° to 144° C. Two recrystallisations from toluene/ethanol 1:4 (fuller's earth) yield 3.3 g (44.6% of theory) of pale, greenish yellow felted needles with a melting point of 143° to 143.5° C.

Analysis: $C_{21}H_{13}NO$ (295.32): calculated: C: 85.40, H: 4.44, N: 4.74; found: C: 85.13, H: 4.38, N: 4.69.

The following β-(dibenzofuran-3-yl)-cyano-styrene derivatives can be manufactured in similar manner:

(15) β-(dibenzofuran-3-yl)-4-cyano-styrene; melting point: 251° to 252° C.
(16) β-(dibenzofuran-3-yl)-2-methyl-4-cyano-styrene; melting point: 178° to 178.5° C.

EXAMPLE 4

8.3 g of the Schiff's base from 2-(4-formyl-phenyl)-benzo[b]furan and p-chloro-aniline of the formula

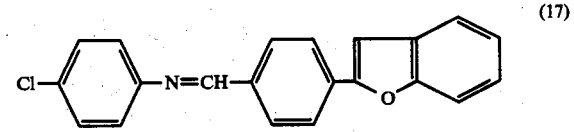
(17)

(melting point: 244° to 245° C., phase transition point: 225° to 226° C.), 2.93 g of p-tolunitrile and 2.7 g of sodium methylate are reacted in 100 ml of dimethyl formamide according to the particulars of Example 1. Yield 7.4 g (92.5% of theory) of 4-cyano-4'-(benzo[b]furan-2-yl)-stilbene of the formula

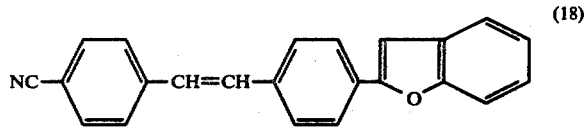

(18)

as yellow flakes with a melting point of 314° to 315° C. (phase transition point: 264° to 265° C.). Two recrystallisations from xylene (fuller's earth) yield 6.2 g (77.5% of theory) of light, greenish yellow, fine flakes with a melting point of 333° to 334° C. (phase transition point: 268° to 269° C.).

Analysis: $C_{23}H_{15}NO$ (321.36): calculated: C: 85.96, H: 4.71, N: 4.36; found: C: 85.72, H: 4.64, N: 4.25.

The following 4'-(benzo[b]furan-2-yl)-stilbene derivatives can be manufactured in similar manner:
(19) 2-cyano-4'-(benzo[b]furan-2-yl)-stilbene melting point: 199.5° to 200° C.
(20) 2-methyl-4-cyano-4'-(beno[b]furan-2-yl)-stilbene melting point: 250° to 251° C.
(21) 2 cyano-4-chloro-4'-(benzo[b]furan-2-yl)-stilbene.
(22) 2-cyano-5-chloro-4'-(benzo[b]furan-2-yl)-stilbene.

The Schiff's base of the formula(17) can be manufactured by fusing together the aldehyde of the formula

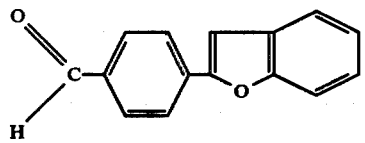

with p-chloroanile (5% excess) over the course of 30 minutes at 190° to 195° C. in an atmosphere of nitrogen and while distilling off the water which forms.

The aldehyde required as starting product is obtained from the corresponding bromomethyl compound by refluxing it for several hours with hexamethylene-tetramine in chloroform and saponifying the quaternary ammonium salt with 50% acetic acid. The bromomethyl compound can in turn be obtained by refluxing the corresponding p-tolyl-substituted compound for several hours with N-bromosuccinimide and catalytic amounts of α,α'-azo-isobutyronitrile in carbon tetrachloride.

EXAMPLE 5

8.3 g of the Schiff's base from 2-phenyl-6-formyl-benzo[b]furan and p-chloroaniline of the formula

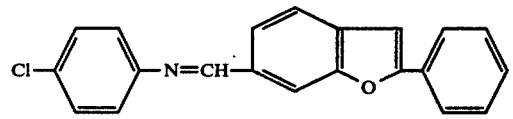

(23)

(melting point: 185° to 186° C.), 2.93 g of p-tolunitrile and 2.7 g of sodium methylate are stirred in 100 ml of dimethyl formamide for 16 hours at 20° to 25° C. with the exclusion of air and processed according to the particulars of Example 1. Yield: 7.6 g (95% of theory) of 2-phenyl-6-(p-cyano-styryl)benzo[b]furan of the formula

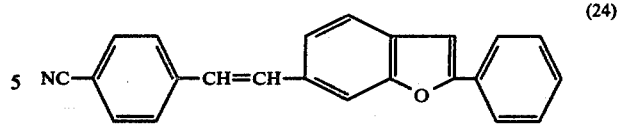

(24)

as a yellow powder with a melting point of 231° to 232° C. Two recrystallisations from toluene (fuller's earth) yield 6.6 g (82.5% of theory) of light yellow, fine, felted needles with a melting point of 233° to 234° C.

Analysis: $C_{23}H_{15}NO$ (321.36): calculated: C: 85.96, H: 4.71, N: 4.36; found: C: 85.78, H: 4.71, N: 4.25.

It is also possible to manufacture 2-phenyl-6-(o-cyano-styryl)benzo[b]furan (25) in similar manner; melting point 164.5°–165° C.

EXAMPLE 6

7.64 g of the Schiff's base from dibenzofuran-3-carbaldehyde an p-chloroaniline of the formula (13), 3.79 g of 3-chloro-4 methyl-benzonitrile and 5.4 g of sodium methylate are stirred in 80 ml of dimethyl formamide for 60 minututes at 20° to 25° C. with the exclusion of air and processed according to the particulars of Example 1. Yield: 4.3 g (52.2% of theory) of β-(dibenzofuran-3-yl)-2-chloro-4-cyano-styrene of the formula

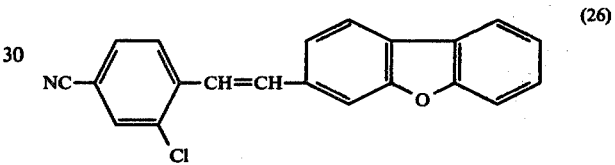

(26)

in the form of yellow needles with a melting point of 211° to 212° C. Two recrystallisations from xylene (fuller's earth) yield 3.55 g (43.1% of theory) of greenish yellow, felted needles with a melting point of 214° to 215° C.

Analysis: $C_{21}H_{12}ClNO$ (329.79): calculated: C: 76.48, H: 3.67, N: 4.25; found: C: 76.30, H: 3.77, N: 4.20.

It is also possible to manufacture 2-chloro-4-cyano-4'-phenyl-stilbene (27) in similar manner: melting point: 191° to 191.5° C.

EXAMPLE 7

5.37 g of the Schiff's base from 2 moles of o-chloroaniline and 1 mole of diphenyl-4,4'-dicarbaldehyde of the formula

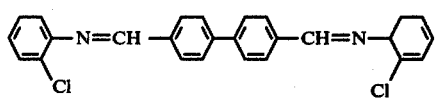

(28)

(melting point: 187.5° to 188° C.) and 2.93 g of p-tolunitrile are dissolved with stirring in 150 ml of dimethyl formamide and the resultant solution is then cooled to 20° C. After displacement of the air by nitrogen, 2.7 g of sodium methylate are added and the reaction mixture is stirred for 16 hours at 20° to 25° C. excluding air, in the course of which a dark violet colouration occurs gradually. Then 600 ml of methanol are added. The mixture is cooled to 0° to 5° C. and the precipitated product is then filtered off with suction, washed with 100 ml of methanol and dried. Yield: 4.08 g (80% of theory) of 4,4'-di-(p-cyano-styryl)-biphenyl of the formula

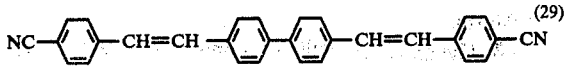
(29)

as a brownish yellow powder with a melting point of 269° to 270° C. Two recrystallisations from o-dichlorobenzene (fuller's earth) yield 3.2 g (63.9% of theory) of light, greenish yellow, glistening needles and spikes which melt at 276° to 277° C.

Analysis: $C_{30}H_{20}N_2$ (408.48): calculated: C: 88.21, H: 4.94, N: 6.86; found: C: 87.90, H: 4.97, N: 6.75.

The following, 4,4'-distyryl-biphenyl derivatives can be manufactured in similar manner:
(30) 4,4'-di-(o-cyano-styryl)-biphenyl; melting point 274° to 275° C.
(31) 4,4'-di-(2-cyano-4-chloro-styryl)-biphenyl; melting point 281° to 282° C.
(32) 4,4'-di-(2-methyl-4-cyano-styryl)-biphenyl; melting point 249° to 250° C.
(33) 4,4'-di-(2-cyano-5-methoxy-styryl)-biphenyl;
(34) 4,4'-di-(3-chloro-4-cyano-styryl)-biphenyl;
(35) 4,4'-di-(3-methoxy-4-cyano-styryl)-biphenyl.

EXAMPLE 8

With stirring 5.37 g of the Schiff's base from 2 moles of o-chloroaniline and 1 mole of 4,4'-dicarbaldehyde of the formula (28) and 3.79 g of 3-chloro-4-methyl-benzonitrile are dissolved in 50 ml of dimethyl formamide and the resultant solution is then cooled to 20° C. After displacement of the air by nitrogen, 5.4 g of sodium methylate are added. The reaction product begins to precipitate after about 30 seconds. The reaction is brought to completion by stirring for about 30 minutes at 20° to 25° C. Then 600 ml of methanol are added and the reaction mixture is cooled to 0° to 5° C. The product which has precipitated is filtered off by suction, washed with 100 ml of methanol and dried. Yield: 5.1 g (=85.5% of theory) of 4,4'-di-(2-chloro-4-cyano-styryl)-biphenyl of the formula

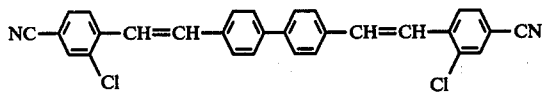

as a yellow powder with a melting point of 283° to 284° C. Two recrystallisations from o-dichlorobenzene (fuller's earth) yield 3.4 g (=57% of theory) of fine, greenish yellow crystals with a melting point of 296° to 297° C.

Analysis: $C_{30}H_{18}Cl_2N_2$ (477.40): calculated: C: 75.48, H: 3.80, N: 5.87: found: C: 75.23, H: 3.84, N: 5.76.

The following distyryl derivatives can be manufactured in similar manner:
(37) 4,4'-di-(2-cyano-3-chloro-styryl)-biphenyl; melting point: 315° to 316° C.
(38) 4,4'-di-(2-cyano-5-chloro-styryl)-biphenyl; melting point: 299° to 300° C.
(39) 1,4-di-(2-chloro-4-cyano-styryl)-benzene; melting point: 299° to 300° C.
(40) 1,4-di-(2-cyano-3-chloro-styryl)-benzene; melting point 314° to 315° C.
(41) 1,4-di-(2-cyano-5-chloro-styryl)-benzene; melting point: 309° to 310° C.
(42) 2,5-di-(2-chloro-4-cyano-styryl)-naphthalene; melting point: >360° C.
(43) 2,6-di-(2-cyano-3-chloro-styryl)-naphthalene; melting point: 354° to 355° C.
(44) 2,6-di-(2-cyano-5-chloro-styryl)-naphthalene; melting point 358° to 359° C.

EXAMPLE 9

A polyester fabric (e.g. "Dacron") is padded at room temperature (ca. 20° C.) with an aqueous dispersion that contains per liter 1 to 2 g of 2-cyano-4'-(benzo[b]furan-2-yl)-stilbene an 1 g of an addition product of about 8 moles of ethylene oxide with 1 mole of p-tert. octylphenol, then dried at about 100° C. The dry material is subsequently subjected to a heat treatment at 150° to 220° C. which lasts from 2 minutes to several seconds, depending on the temperature. The treated material exhibits an outstanding white effect of good fastness to light.

EXAMPLE 10

100 g of polyester granules of terephthalic acid ethylene glycol polyester are intimately mixed with 0.05 g of one of the compounds of the formulae (18) or (19) and the mixture is fused at 285° C. with stirring. The melt is spun through conventional spinnerets to yield strongly brightened polyester fibres. It is also possible to add the compounds of the formulae (18) or (19) to the starting materials before or during the polycondensation the the polyester.

EXAMPLE 11

100 g of polypropylene "Fibre-Grade" are intimately mixed with 0.8 g of the compound of the formula (11) and the mixture is fused at 280° to 290° C. with stirring. The melt is spun through conventional spinnerets by melt spinning methods which are known per se and stretched. Conspicuously brightened polypropylene fibers are obtained.

EXAMPLE 12

100 g of polyester granules of terephthalic acid ethylene glycol polyester are intimately mixed with 0.05 g of one of the compounds of the formulae (29), (30), (31), (32), (37) or (38) and the mixture is melted with stirring at 285° C. The melt is spun through conventional spinnerets to yield highly brightened polyester fibres.

It is also possible to add the above mentioned compounds to the starting materials before or during the polycondensation to give the polyester.

We claim:
1. Cyano-substituted stilbene compounds of the formula

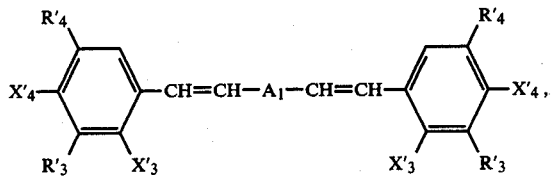

wherein $A_1$ represents 1,4-, 1,5- or 2,6-naphthylene, 1,4-phenylene or 4,4'- bis-phenylene, one of the symbols $X'_3$ and $X'_4$ represents the cyano radical and the other represents hydrogen or chlorine, and each of $R'_3$ and $R'_4$ independently represents hydrogen or chlorine, and at least one, and at most two, of the symbols $X'_3$, $X'_4$, $R'_3$ and $R'_4$ represents chlorine.

2. Cyano-substituted stilbene compounds according to claim 1 of the formula

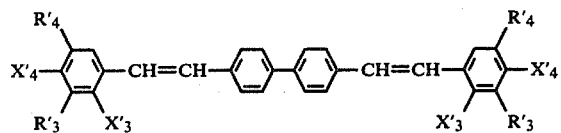

wherein one of the symbols X'$_3$ and X'$_4$ represents the cyano radical and the other represents hydrogen or chlorine, and each of R'$_3$ and R'$_4$ independently represents hydrogen or chlorine, and at least one, and at most two, of the symbols X'$_3$, X'$_4$, R'$_3$ and R'$_4$ represents chlorine.

3. Cyano-substituted stilbene compounds according to claim 1 of the formula

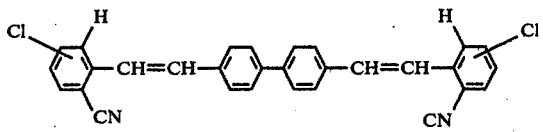

* * * * *